United States Patent
Voegele et al.

(10) Patent No.: US 6,261,302 B1
(45) Date of Patent: Jul. 17, 2001

(54) APPLIER FOR IMPLANTABLE SURGICAL MARKER

(75) Inventors: James W. Voegele; Michael E. Boehm, both of Cincinnati; Russell L. Holscher, West Chester, all of OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/105,570

(22) Filed: Jun. 26, 1998

(51) Int. Cl.$^7$ .................................................... A61B 17/04
(52) U.S. Cl. .......................... 606/151; 606/142; 128/749
(58) Field of Search ................................. 606/151, 142, 606/143, 219, 116, 117; 128/749

(56) References Cited

U.S. PATENT DOCUMENTS

| | | |
|---|---|---|
| 2,549,731 | 4/1951 | Wattley . |
| 3,150,379 | 9/1964 | Brown . |
| 4,080,959 | 3/1978 | Leveen ................................ 128/2 H |
| 4,399,810 | 8/1983 | Samuels et al. ...................... 128/337 |
| 4,407,283 | 10/1983 | Noiles et al. ......................... 128/334 |
| 4,505,273 | 3/1985 | Braun et al. .......................... 128/335 |
| 4,607,638 | 8/1986 | Crainich ............................... 128/335 |
| 4,649,151 | 3/1987 | Dougherty et al. .................. 514/410 |
| 4,733,664 | 3/1988 | Kirsch et al. ......................... 128/334 |
| 4,762,260 | 8/1988 | Richards et al. ....................... 227/19 |
| 4,874,122 | 10/1989 | Froelich et al. ........................ 227/19 |
| 4,983,176 | 1/1991 | Cushman et al. ..................... 606/151 |
| 5,147,307 | 9/1992 | Seymourr .............................. 604/116 |
| 5,192,270 | 3/1993 | Carswell, Jr. ......................... 604/116 |
| 5,221,269 | 6/1993 | Miller et al. .......................... 604/281 |
| 5,222,975 | 6/1993 | Crainich ............................... 606/219 |
| 5,240,011 | 8/1993 | Assa ..................................... 128/751 |
| 5,246,156 | 9/1993 | Rothfuss et al. ...................... 227/176 |
| 5,366,479 | 11/1994 | McGarry et al. ..................... 606/219 |
| 5,782,775 | 7/1998 | Milliman et al. ..................... 600/567 |

FOREIGN PATENT DOCUMENTS

WO9608208A1  3/1996  (WO) .

OTHER PUBLICATIONS

Sandra S. Kramer, M.D. et al. "A Permanent Radiopaque Marker Technique for the Study fo Pharyngeal Swallowing in Dogs" Dysphagia 1:163–167 (1987).

*Primary Examiner*—Gary Jackson
(74) *Attorney, Agent, or Firm*—Matthew S. Goodwin

(57) ABSTRACT

An applier for delivering and deploying a biopsy marker to a surgical biopsy site is disclosed. The applier has a ferrule with a forming surface to form the marker on the distal end of a flexible tube. The marker is held at the distal end of the flexible tube in a marker holder. A forming rod slidable in the flexible tube urges the marker into contact with the forming surface of the ferrule for marker formation. The distal end of the flexible tube is delivered through an egress tube, which in turn is delivered through a biopsy cannula adapted for taking the biopsy sample. The egress tube has an alignment hub at its proximal end adapted for orientational alignment with a hub receiver on the biopsy cannula. When properly aligned, the egress opening of the distal end of the egress tube is orientationally aligned with the biopsy port of the biopsy cannula for proper delivery and deployment of the marker.

8 Claims, 17 Drawing Sheets

APPLIER FOR IMPLANTABLE SURGICAL MARKER

BACKGROUND OF THE INVENTION

This invention relates to an applier for delivering and deploying a marker for implantation in tissue of a surgical patent More specifically, it relates to such an applier for delivery and deployment of an implantable biopsy marker for defining particular locations in human tissue during a biopsy procedure, particularly in a human breast.

One in nine American women will develop breast cancer in their lifetime. It is the leading cause of cancer deaths in women 40–55 years of age and the second leading cause of cancer deaths in women overall. Breast cancer will be diagnosed in approximately one in eight women in their lifetime, and one in 30 will die of this disease. Breast cancer does occur in males but is much less common. Biopsy requests stem from a screening process generally performed via a physical examination (palpable) and/or mammogram (non-palpable). A biopsy is indicated if suspicious tissue is detected. Five out of six biopsies performed return benign indications.

It is desirable and often necessary to perform procedures for detecting, sampling, and testing lesions and other abnormalities in the tissue of humans and other animals, particularly in the diagnosis and treatment of patients with cancerous tumors, pre-malignant condition and other diseases or disorders. Typically, in the case of cancer, when a physician establish by means of known procedures (i.e. palpation, x-ray, MRI, or ultrasound imaging) that suspicious circumstances exist, a biopsy is performed to determine whether the cells are cancerous. Biopsy may be an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In FNA biopsy, very small needles are used to obtain individual cells or clusters of cells for cytologic examination. The cells may be prepared such as in a Papanicolaou (Pap) smear. In core biopsy, as the term suggests, a core or fragment of tissue is obtained for histologic examination, which may be done via a frozen section or paraffin section. The chief difference between FNA and core biopsy is the size of the tissue sample taken. An imaging system having spectroscopic capabilities, such as the stereotactic guidance system described in U.S. Pat. No. 5,240,011 is employed to guide the extraction instrument to the lesion.

Depending on the procedure being performed, the sample may result in the suspicious lesion being partially or completely removed. Visibility of the lesion by the imaging system may be hampered because of the distortion created by the extraction process itself as well as associated bleeding in the surrounding tissues. Although the lesion is removed and all fluids are continuously aspirated from the extraction site, it is likely that the process will "cloud" the lesion, thus impairing exact recognition of its margins. This makes it difficult to ensure that the entire lesion will be removed.

Often, the lesion is merely a calcification derived from dead abnormal tissue, which may be cancerous or pre-cancerous, and it is desirable to remove only a sample of the lesion, rather than the entire lesion, to evaluate it. This is because such a lesion actually serves to mark or define the location of adjacent abnormal tissue, so the physician does not wish to remove the entire lesion and thereby lose a critical means for later relocating the affected tissue. One of the benefits to the patient from core biopsy is that the mass of the tissue taken is small. However, oftentimes, either inadvertently or because the lesion is too small, the entire lesion is removed for evaluation, even though it is desirable to remove only a portion. Then, if subsequent analysis indicates the tissue to be malignant (malignant tissue requires removal, days or weeks later, of tissue around the immediate site of the original biopsy), it is difficult for the physician to determine the precise location of the lesion, in order to perform necessary additional procedures on adjacent potentially cancerous tissue. Additionally, even if the lesion is found to be benign, there will be no evidence of its location during future examinations, to mark the location of the previously removed calcification so that the affected tissue may be carefully monitored for future reoccurrence.

Thus, it would be of considerable benefit to be able to permanently mark the location or margins of such a lesion prior to or immediately after removing the sample. Marking prior to removal would help to ensure that the entire lesion is excised, if desired. Alternatively, if the lesion were inadvertently removed in its entirety, marking the biopsy site immediately after the procedure would enable reestablishment of its location for future identification.

A number of procedures and devices for marking and locating particular tissue locations are known in the prior art. For example, location wire guides, such as that described in U.S. Pat. No. 5,221,269 to Miller et al, are well known for locating lesions, particularly in the breast. The device described by Miller comprises a tubular introducer needle and an attached wire guide, which has at its distal end a helical coil configuration for locking into position about the targeted lesion. The needle is introduced onto the breast and guided to the lesion site using an imaging system of a known type, for example, x-ray, ultrasound or magnetic resonance imaging (MRI), at which time the helical coil at the distal end is deployed about the lesion. Then, the needle may be removed from the wire guide, which remains in a locked position distally about the lesion for guiding a surgeon down the wire to the lesion site during subsequent surgery. While such a location system is effective, it is obviously intended and designed to be only temporary, and is removed once the surgery or other procedure has been completed.

Other devices are known for marking external regions of a patient's skin. For example, U.S. Pat. No. 5,192,270 to Carswell, Jr. discloses a syringe which dispenses a colorant to give a visual indication on the surface of the point at which an injection has or will be given. Similarly, U.S. Pat. No. 5,147,307 to Gluck discloses a device which has patterning elements for impressing a temporary mark in a patients skin, for guiding the location of an injection or the like. It is also known to tape or otherwise adhere a small metallic marker, e.g. a 3 millimeter diameter lead sphere, on the skin of a human breast in order to delineate the location of skin calcifications (see Homer et al, The Geographic Cluster of Microcalcifications of the Breast, Surgery, Gynecology, & Obstetrics, December 1985). Obviously, however, none of these approaches are useful for marking and delineating internal tissue abnormalities, such as lesions or tumors.

Still another approach for marking potential lesions and tumors of the breast is described in U.S. Pat. No. 4,080,959. In the described procedure, the skin of the portion of the body to be evaluated, such as the breasts, is coated with a heat sensitive color-responsive chemical, after which that portion of the body is heated with penetrating radiation such as diathermy. Then, the coated body portion is scanned for color changes which would indicate hot spots beneath the skin surface. These so-called hot spots may represent a tumor or lesion, which does not dissipate heat as rapidly because of its relatively poor blood circulation (about 1/20 of the blood flow through normal body tissue). This method, of course, functions as a temporary diagnostic tool, rather than in a permanent means for delineating the location of a tumor or lesion.

A method of identifying and treating abnormal neoplastic tissue or pathogens within the body is described in U.S. Pat. No. 4,649,151 to Doughety et al. In this method, a tumor-selective photosensitizing drug is introduced into a patient's body, where it is cleared from normal tissue faster than it is cleared from abnormal tissue. After the drug clears normal tissue but before it has cleared abnormal neoplastic tissue, the abnormal neoplastic tissue may be located by the luminescence of the drug within the abnormal tissue. The fluorescence may be observed with low intensity light, some of which is within the drug's absorbency spectrum. Once detected, the tissue may be destroyed by further application of higher intensity light having a frequency within the absorbency spectrum of the drug. Of course, this method also is only a temporary means for marking the abnormal tissue. Additionally, once the abnormal tissue has been destroyed during treatment, the marker is destroyed as well.

It is also known to employ biocompatible dyes or stains to mark breast lesions. First, a syringe containing the colorant is guided to a detected lesion, using an imaging system. Later, during the extraction procedure, the surgeon harvests a tissue sample from the stained tissue. However, while such staining techniques can be effective, it is difficult to precisely localize the stain. Also, the stains are difficult to detect flouoroscopically and may not always be permanent.

Additionally, it is known to implant markers directly into a patient's body using invasive surgical techniques. For example, during a coronary artery bypass graft (CABG), which of course constitutes open-heart surgery, it is common practice to surgically apply one or more metallic rings to the aorta at the site of the graft. This enables a practitioner to later return to the site of the graft by identifying the rings, for evaluative purposes. It is also common practice to mark a surgical site with staples, vascular clips, and the like, for the purpose of future evaluation of the site.

A technique has been described for the study of pharyngeal swallowing in dogs, which involves permanently implanting steel marker beads in the submucosa of the pharynx (S. S. Kramer et al, A Permanent Radiopaque Marker Technique for the Study of Pharyngeal Swallowing of Dogs, Dysphagia, Vol. 1, pp.163–167, 1987). The article posits that the radiographic study of these marker beads during swallowing on many occasions over a substantial period of time provides a better understanding of the pharyngeal phase of deglutition on humans. In the described technique, the beads were deposited using a metallic needle cannula having an internal diameter slightly smaller than the beads to be implanted. When suction was applied to the cannula, the bead sat firmly on the tip. Once the ball-tipped cannula was inserted through tissue, the suction was broken, thereby releasing the bead, and the cannula is withdrawn.

Of course, this technique was not adapted or intended to mark specific tissue sites, but rather to mark an entire region or structure of the body in order to evaluate anatomical movements (i.e. swallowing motions). It also was not intended for use in humans.

Accordingly, what is needed is a method and device for non-surgically implanting potentially permanent markers at the site of a lesion or other abnormal tissue, for the purpose of defining the margins of a lesion before it is removed and/or to establish its location after it has been removed. The markers should be easy to deploy and easily detected using state of the art imaging techniques.

A method of implanting markers directly into a patient's body using minimally invasive surgical techniques is described in International Patent No. WO 9608208A1 to Foerster et al. In this method, a clipping device is introduced to the lesion site by a tubular cannula. Once the clip is at the lesion site, an actuating means at the proximal end outside the patient deploys the clip into the tissue. This marking means can be used long term and can be imaged by most imaging techniques. However, because of it's small size, current ultrasound imaging systems are unable to detect is within the tissue.

Another method of implanting a marker is described in copending, commonly assigned application Ser. No. 08/802, 958, filed Feb. 21, 1997, and entitled "Apparatus and Method for Marking Tissue". The marker described in this method utilizes a central tang that is tensily loaded to cause a squarely supported, end contact bridge on the marker to bend resulting in the goal post arms to swing inward in an arcuate fashion to pinch tissue. The tensile load on the tang is increased until it breaks at a predetermined location leaving the marker attached to the tissue site. Unfortunately, this method requires the marker to be pulled away from tissue when the marker is formed, consequently, limiting marker penetration and the amount of tissue grasped. Additionally, the marker is delivered to the biopsy site when the marker applier is correspondingly delivered through the biopsy cannula which is used for taking the biopsy sample. It is necessary to properly orient the opening on the applier with the biopsy port on the biopsy cannula in order to properly deploy the marker at the biopsy site. Unfortunately, the method described in this pending application does not describe a technique for readily accomplishing the proper orientational alignment between the applier opening and the biopsy port A surgical clip for permanently joining opposed tissue for an anastomosis procedure is described in U.S. Pat. No. 4,733,664 to Kirsh et al. This is accomplished using an applier, also disclosed, to pull on a frangible central tang to close a pair of spaced arcuate arms extending generally parallel in one direction from opposite ends of the plastically deformable bridge. The arms are brought around opposed tissue. A predetermined force is applied to create a tensile break of the neck in the tang. Specific angles of clip shoulder and applier are given. The applier jaw faces are in the range of 120° to 180° with respect to one another, specifically 150° Unfortunately, the method of forming this clip suffers a fate similar to the method described in the preceding paragraph.

Accordingly, what is needed is an applier for delivering a biopsy marker to a site of a surgical biopsy, and deploying the marker at the site. The applier should be capable of forming the marker from an original open configuration to a closed configuration at the biopsy site. It should be able to accomplish this forming function simply and reliably. Additionally, the applier should be capable of readily aligning the opening in the applier which delivers the marker with the biopsy port of the biopsy cannula which takes the biopsy sample to ensure proper deployment of the marker.

SUMMARY OF INVENTION

The invention is an applier for initially delivering a biopsy marker to a surgical biopsy site and subsequently deploying the marker at the site. The applier comprises an elongated flexible tube having a distal end, a ferrule fixed to the distal end of the flexible tube, a marker holder at the ferrule for holding the biopsy marker at the distal end of the flexible tube in the original open position, an elongated forming rod, and an egress tube for receiving the distal end of the elongated flexible tube.

The ferrule of the applier has a forming surface on it adapted to reconfigure the biopsy marker from an original open configuration to a closed configuration when the biopsy marker has been delivered to the surgical site.

The elongated forming rod in the flexible tube is adapted to urge the biopsy marker into reconfiguring contact with the forming surface of the ferrule. The forming rod is slidable in the flexible tube from an unactuated position where the biopsy marker is in the original open position to an actuated position where the biopsy marker has been reconfigured in the closed position (and consequently deployed at the surgical site).

The egress tube of the applier is adapted for delivery through a biopsy cannula. The biopsy cannula has a biopsy port at its distal end. During a biopsy, the biopsy port of the biopsy cannula is positioned at the biopsy site so that a biopsy sample can be captured in the port. The egress tube has proximal and distal ends. The egress tube has an egress opening at egress tube has proximal and distal ends. The egress tube has an egress opening at the distal end of the egress tube. It also has an alignment hub at its proximal end. The alignment hub is adapted for orientational alignment with a hub receiver on the biopsy cannula. The alignment of the alignment hub and the hub receiver causes the alignment of the egress opening of the egress tube with the biopsy port of the biopsy cannula.

The applier of this invention delivers a biopsy marker to a site of a surgical biopsy, and deploys the marker at the site. The applier readily forms the marker from an original open configuration to a closed configuration at the biopsy site. This is accomplished by using the forming rod to urge the marker held in the marker holder into reconfiguring contact with the forming surface of the ferrule. Consequently, marker formation is accomplished simply and reliably.

Significantly, the egress opening of the egress tube of the applier of this invention can be readily aligned with a biopsy port of a biopsy cannula. The marker is delivered through the egress opening of the egress tube when the distal end of the elongated flexible tube is delivered through the egress tube. The biopsy sample is taken with the biopsy cannula when the biopsy port is positioned at the biopsy site. When the egress opening of the egress tube and the biopsy port of the biopsy cannula are orientationally aligned in the same direction, the marker can be properly delivered through the egress opening and into the biopsy port of the biopsy cannula. When the marker is delivered into the biopsy port, proper delivery of the marker to the biopsy site has been established, and proper deployment of the marker at the site can accordingly be accomplished. The incorporation of the alignment hub at the proximal end of the egress tube for orientation alignment with a hub receiver on the biopsy cannula provides a simple mechanism to insure proper alignment and thus proper delivery and deployment of the marker at the site.

The applier of this invention can be used in any biopsy procedure where it is necessary or desirable to deliver and deploy a marker at a biopsy site. The applier can be used to deliver and deploy a marker during an endoscopic surgical procedure, or a conventional open surgical procedure as well.

DETAILED DESCRIPTION OF THE PREFERRED EMBODIMENT

The preferred applier 30 for delivering a marker to a biopsy site and subsequently deploying the marker at the site is illustrated in detail in FIGS. 1–9. The preferred marker 31 for the applier can best be seen in FIG. 6. This marker is described in detail in commonly assigned, copending application Ser. No. 09/105,757, filed Jun. 26, 1998. (Attorneys' Docket No. END-536).

Figure 6:
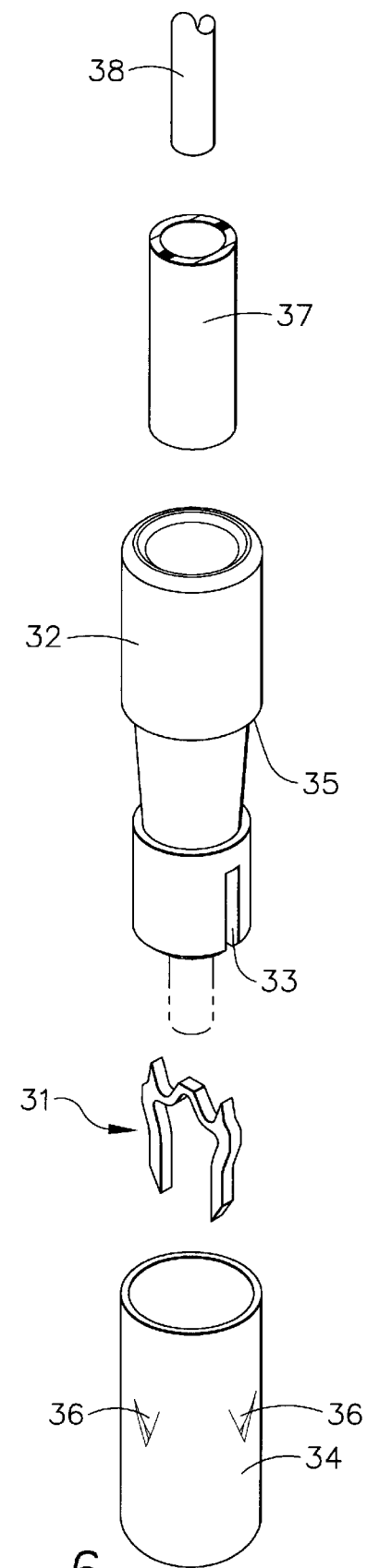
FIG. 6 is an enlarged and exploded isometric view of the distal end of the applier of FIG. 1.
Figure 7:
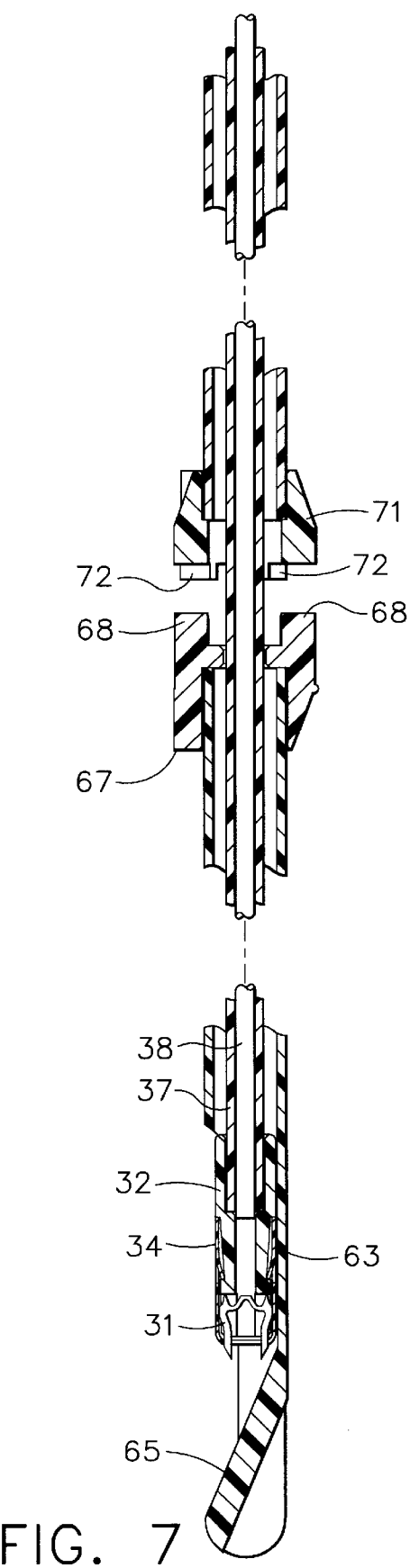
FIG. 7 is a longitudinal section view through the distal end portion of the applier of FIG. 1.
Figure 8:
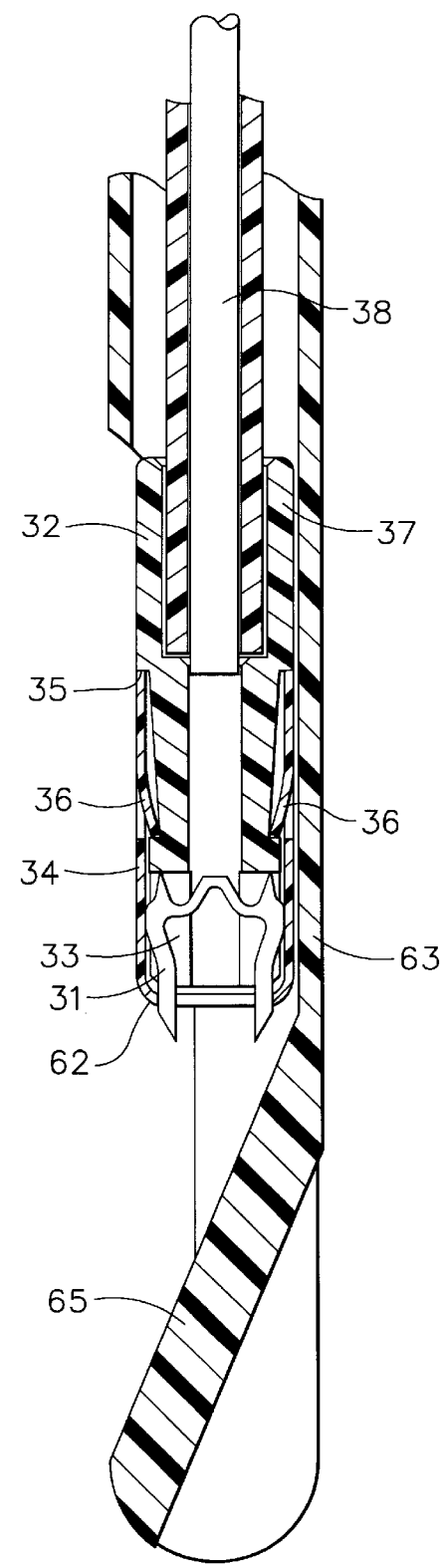
FIG. 8 is an enlarged view of the distal end portion of the applier of FIG. 1.
Figure 9:
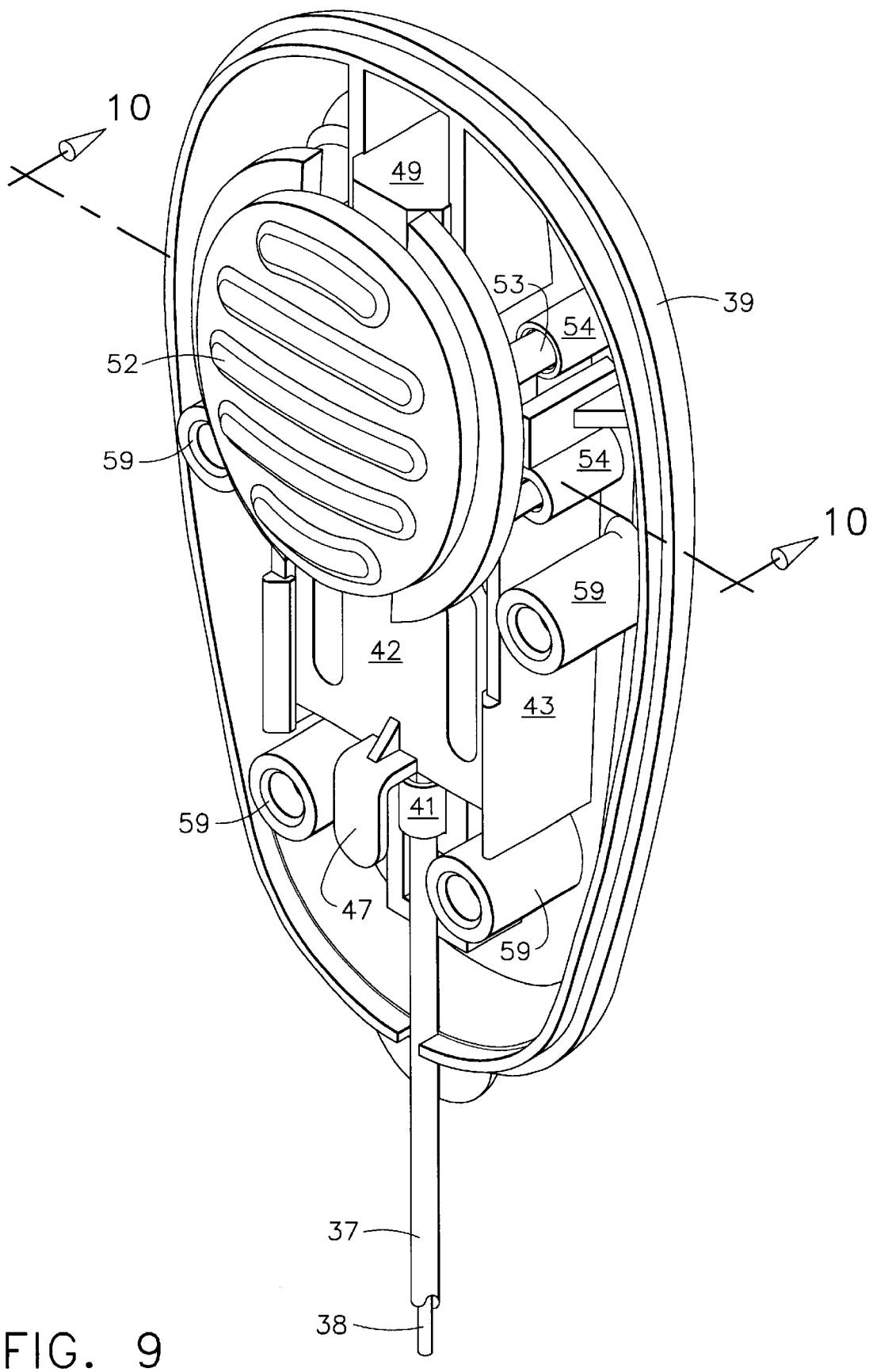
FIG. 9 is an enlarged partially assembled isometric view of the housing portion of the applier of FIG. 1.

As illustrated in FIG. 6, and further aided with FIGS. 7 and 8, the marker is held in its open position within a marker holder 32. The distal portion of the marker holder has a slot 33 for receiving the marker. A ferrule 34 receives the marker holder containing the marker. The proximal end of the ferrule abuts an abutment shoulder 35 on the marker holder, and a plurality of staked cleats 36 ensures secure attachment of the ferrule to the marker holder. As illustrated specifically in FIG. 8, the ferrule has a rolled distal edge forming surface 62 for reconfiguring the marker held in the marker holder from its original open configuration to a closed configuration once the marker has being properly delivered to, and positioned within, the biopsy site.

As illustrated in FIGS. 2, 6, 7 and 8, the marker holder 32 is bonded to the distal end of an elongated flexible tube 37. Consequently, the ferrule is effectively secured to the distal end of the flexible tube. An elongated, push wire forming rod 38 is received in the flexible tube. The forming rod can slide inside the flexible tube and is adapted to reconfigure the marker housed in the marker slot within the ferrule from its original open position to its closed position. In FIGS. 7 and 8, the forming rod is illustrated in an unactuated position within the flexible tube, spaced from the marker.

Referring now to FIGS. 2–4 and 9, the reader will observe that the elongated flexible tube 37 is attached to a housing 39. The flexible tube has a flexible tube base 40 at its proximal end which is secured in a flexible tube cavity 41 within the housing. A slider 42 is received in the housing between a pair of slider tracks 43. The slider has a pair of spring arms 44, each of which includes a slider detent 45. The slider also includes a spring retainer 46 and an indicator tab 47. A spring 48 is seated on the spring retainer and abuts a spring base 49 in the housing when the slider is placed in the housing.

Figure 12:
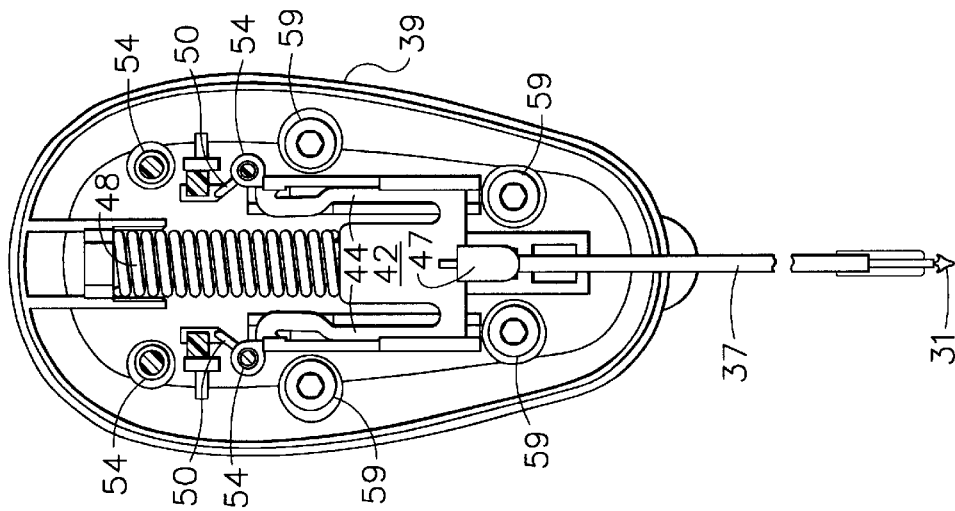
FIG. 12 is a section view taken along line 10—10 of FIG. 9 illustrating the applier in its fired position.
Figure 11:
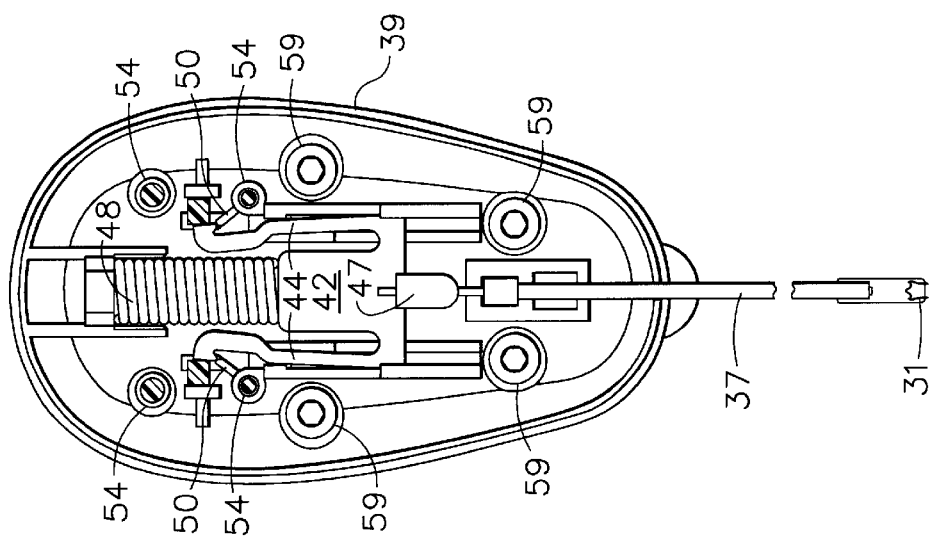
FIG. 11 is a section view taken along line 10—10 of FIG. 9 illustrating the applier at an intermediate point between its pre-fired and fired positions.
Figure 10:
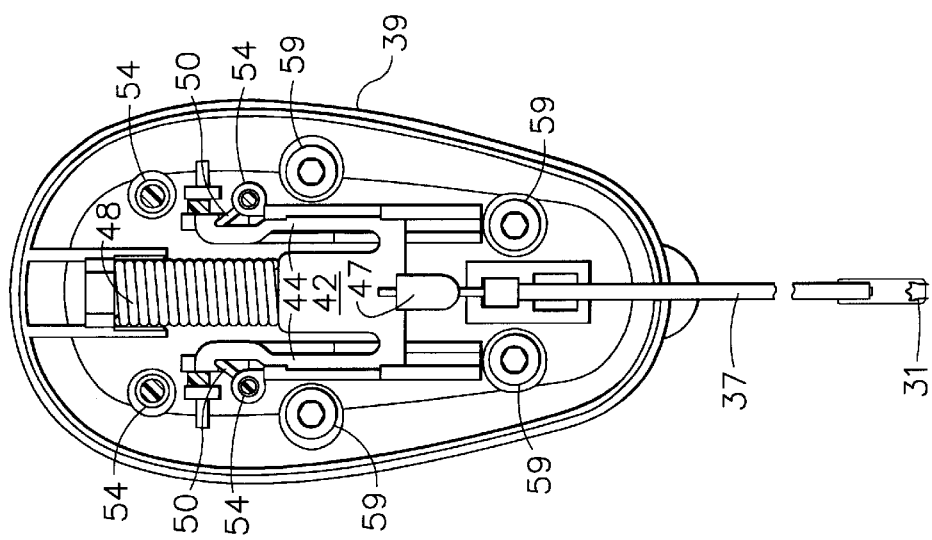
FIG. 10 is a section view taken along line 10—10 of FIG. 9 illustrating the applier in its pre-fire position.

Continuing to refer to FIGS. 2–4 and 9, and further observing FIGS. 10–12, when the slider 42 is positioned between the slider tracks 43 of the housing, the pair of slider detents 45 on the spring arms 44 of the slider rest on a pair of corresponding slide locks 50 contained in the housing. In its unfired position (FIG. 10), the slide locks hold the slider in a proximal position, and the spring is compressed. When the slider is actuated (FIGS. 11 and 12), the slider detents of the spring arms move past the slide locks in the housing, and the slider consequently moves distally as a result of the spring force of the spring.

Figure 4:
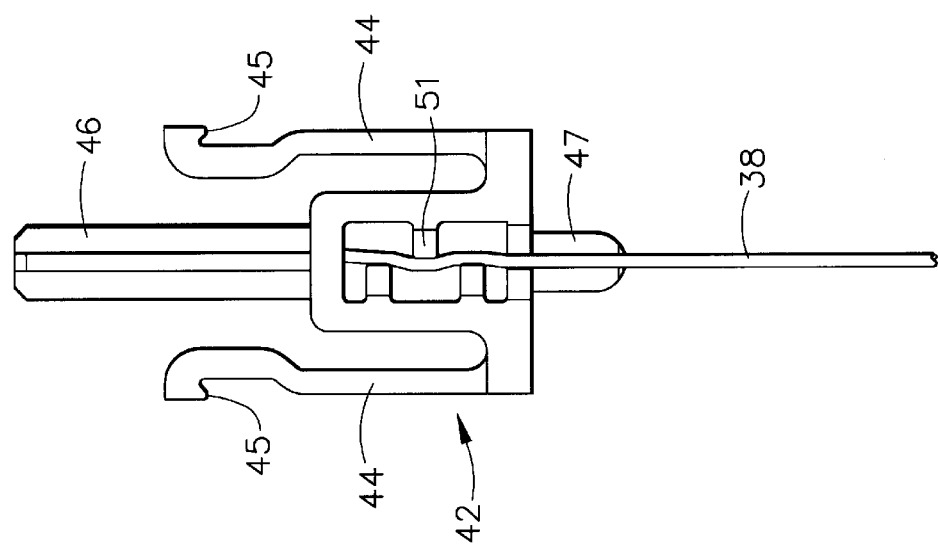
FIG. 4 is a rear elevational view of a slider contained in the housing portion of the applier of FIG. 1 for actuating the forming rod.

As illustrated in FIG. 4, a push wire retainer 51 crimps the proximal end of the elongated push wire forming rod 38 to secure the forming rod to the slider. Consequently, when the slider is actuated as illustrated in FIGS. 10–12, the forming rod moves distally as the slider moves distally so that the distal end of the forming rod engages the marker for reconfiguration of the marker from its original open position to its closed position Referring now to FIGS. 2, 3, and 9, the reader will observe a release button 52 which is attached to the housing. The release button has four guide pins 53 which are received in four corresponding slide guides 54 in the housing. The release button also has a pair of firing posts 55, each of which includes a firing ramp 56 (see specifically FIG. 3). The firing posts of the release button are adapted to contact the spring arms 44 of the slider 42 at the firing ramps when the release button is squeezed. Consequently, when the release button is squeezed, the firing ramps on the firing post of the button urge the spring arms of the slider inwardly as illustrated in FIG. 11. As a result of this inward movement, the slider detents on the spring arms of the slider move past the slider locks 50 in the housing so that the spring force of the spring can urge the slider to move distally.

Figure 1:
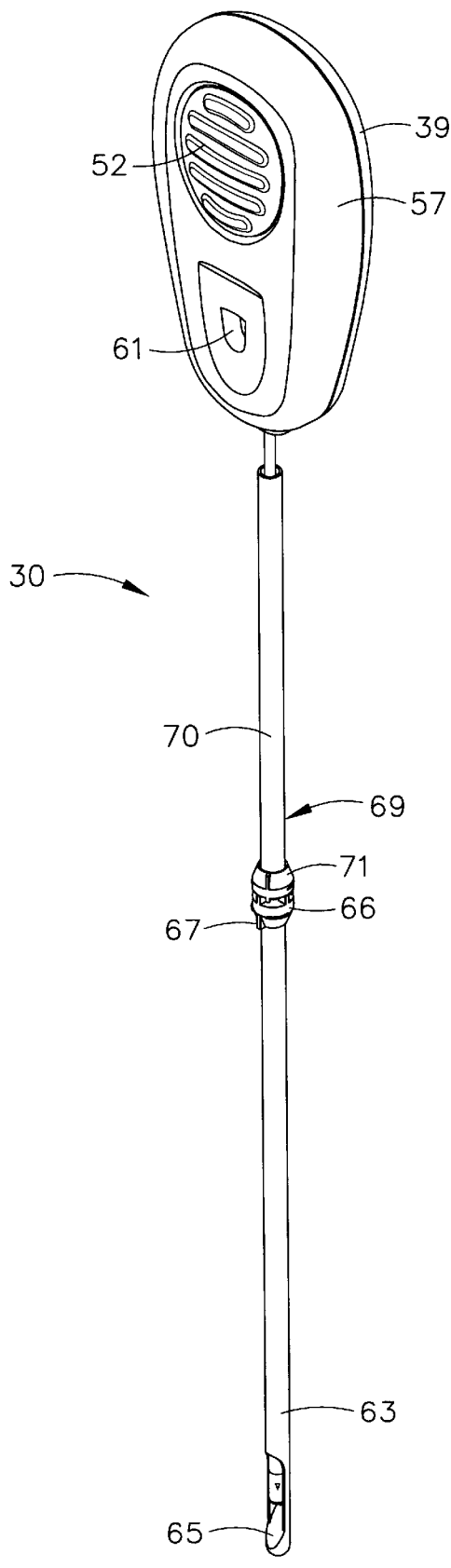
FIG. 1 is and isometric view of an applier for a marker constructed in accordance with a preferred embodiment of this invention.
Figure 2:
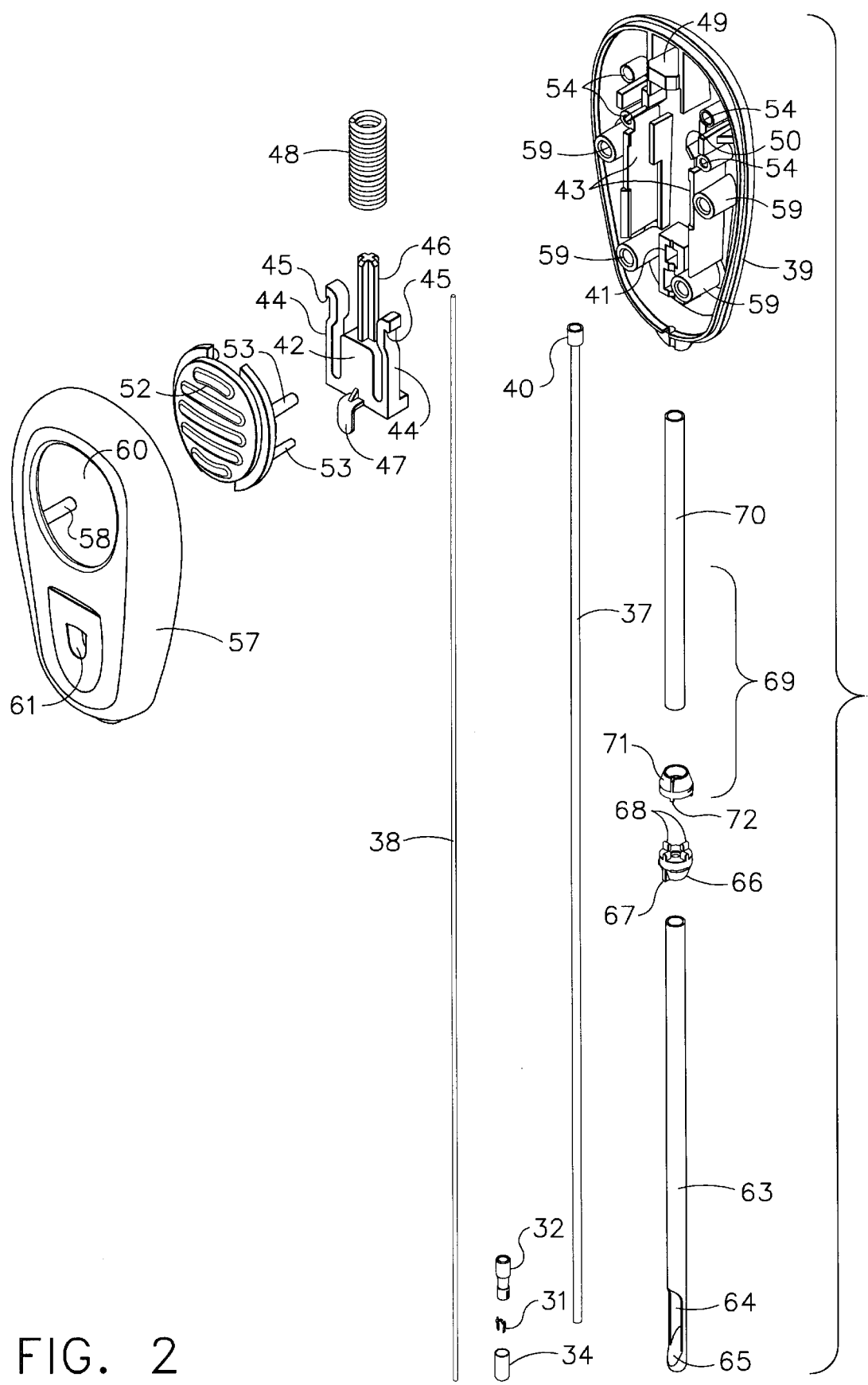
FIG. 2 is an exploded isometric view of the applier of FIG. 1.
Figure 3:
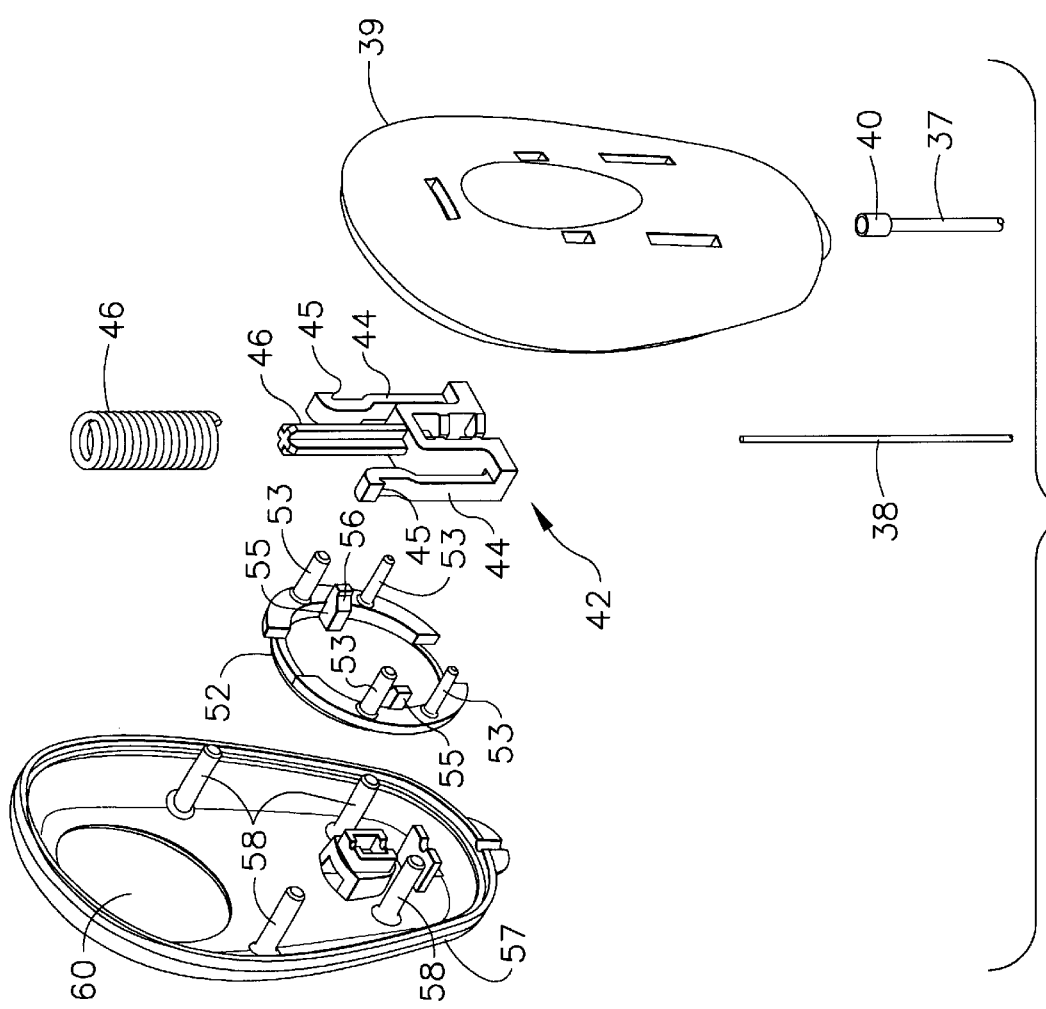
FIG. 3 is an exploded isometric view of the housing portion of the applier of FIG. 1.
Figure 5:
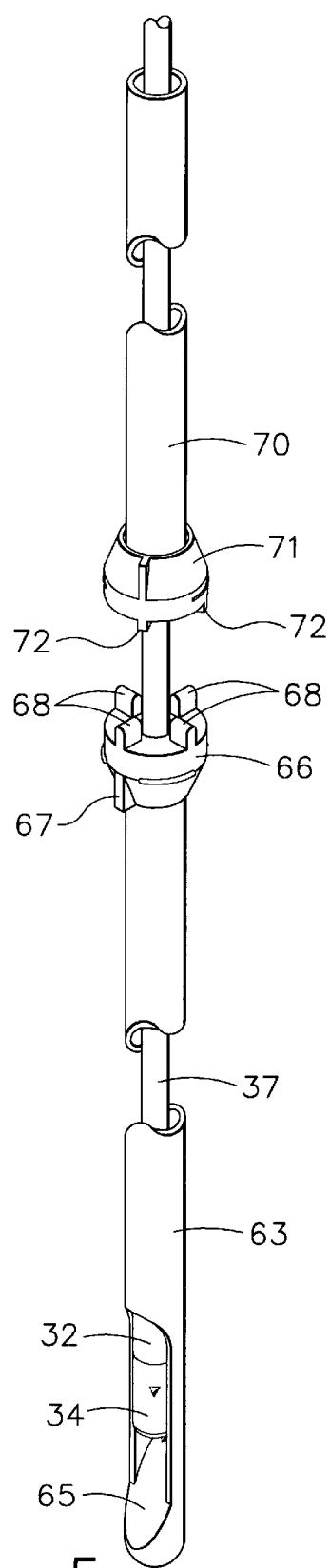
FIG. 5 is an enlarged and foreshortened isometric view of the distal end of the applier of FIG. 1.

As illustrated in FIGS. 2 and 3, the housing has a housing cover 57 to cover the contents within the housing. The housing cover has a plurality of assembly pins 58 which are received in corresponding assembly bosses 59 of the housing. The housing cover also has a button orifice 60 from which orifice 60 from which the release button protrudes when the housing cover is attached to the housing. Finally, the housing cover has a view port 61.

Referring once again to FIGS. 10–12, when the slider 42 is in its unfired position, the release button 52 on the housing of the applier has not yet been squeezed, and the push wire forming rod 38 is in its unactuated position spaced from the marker. When the button is squeezed, the slider moves distally from its unfired position to its fired position. Since the proximal end of the push wire forming rod is attached to the slider, the forming rod moves from its unactuated position to its actuated position when the slider moves from its unfired position to its fired position. When the forming rod moves distally within the flexible tube 37 of the applier, it moves through the marker holder 32 and makes contact with the marker 31. Consequently, upon further distal movement of the forming rod, the marker is cammed against the distal edge forming surface 62 of the ferrule 34 for reconfiguration of the marker from its original open position to its closed position. As seen in FIG. 12, upon complete firing of the marker, the marker and the forming rod protrude form the distal end of the ferrule. Additionally, when the button is squeezed and the slider has moved to the fired position, the indicator tab 47 on the slider is consequently positioned so that it is observable through the view port 61 of the housing cover 57. This provides the user of the applier with a visual indication that the marker has been deployed. This visual indication, coupled with tactile and audible sensations when the release button is squeezed, provides the user with an array of sensory perceptions to ensure that the marker has indeed been fired.

Referring now to FIGS. 2, 5, 7 and 8, the preferred applier of this invention has an egress tube 63 for receiving the distal end of the elongated flexible tube 37. The egress tube has an egress opening 64 at its distal end. The egress opening has an egress ramp 65. At its proximal end, the egress tube has an alignment hub 66. The alignment hub has an alignment tab 67 at its distal end, and two pairs of hub tabs 68 at its proximal end.

In a particularly preferred embodiment of the applier of this invention, the applier has an alignment tool 68 mounted over the elongated flexible tube 37 for sliding and rotational movement between the housing 39 of the applier and the alignment hub 66 on the proximal end of the egress tube 63. The alignment tool has a driver tube 70 for manipulating the alignment tool, and a hub driver 71 affixed to the driver tube at the distal end of the driver tube. The hub driver has four driver tabs 72 at its distal end which are adapted to align with the hub tabs 68 on the proximal end of the alignment hub of the egress tube.

Figure 13:
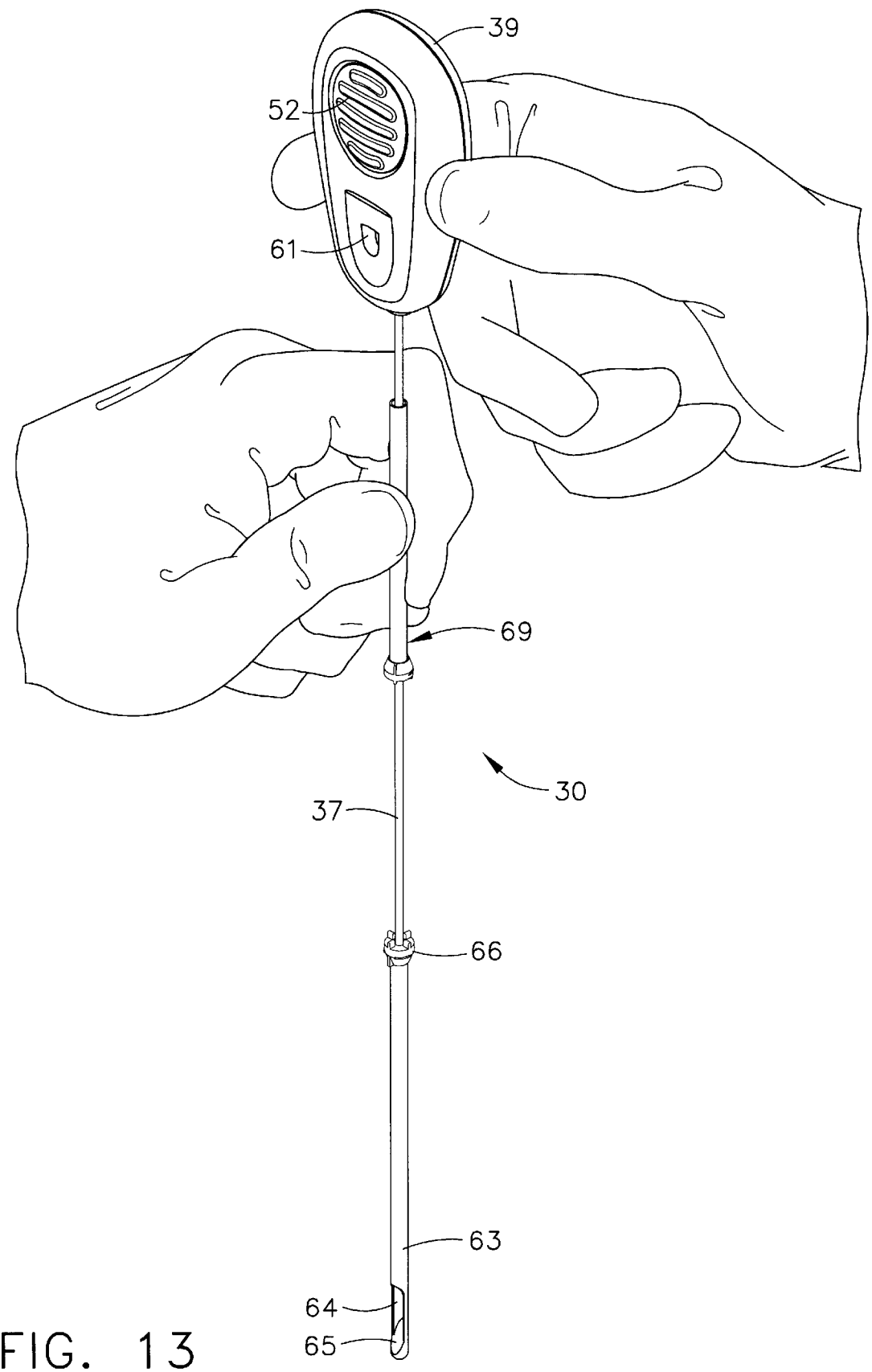
FIG. 13 is an isometric view of the applier of FIG. 1 illustrated pre-operatively where an alignment tool for the applier is being held above the egress tube.

We will now turn to FIGS. 13–27, which illustrate how the applier is used to deliver the marker through a biopsy cannula of a biopsy instrument to a biopsy site for subsequent deployment of the marker at the site. As illustrated specifically in FIG. 13, the user initially threads a portion of the distal end of the flexible tube 37 through the egress tube 63. The reader should note that the alignment tool 69 is positioned around the proximal end of the flexible tube between the egress tube and the housing 39 of the applier.

Figure 14:
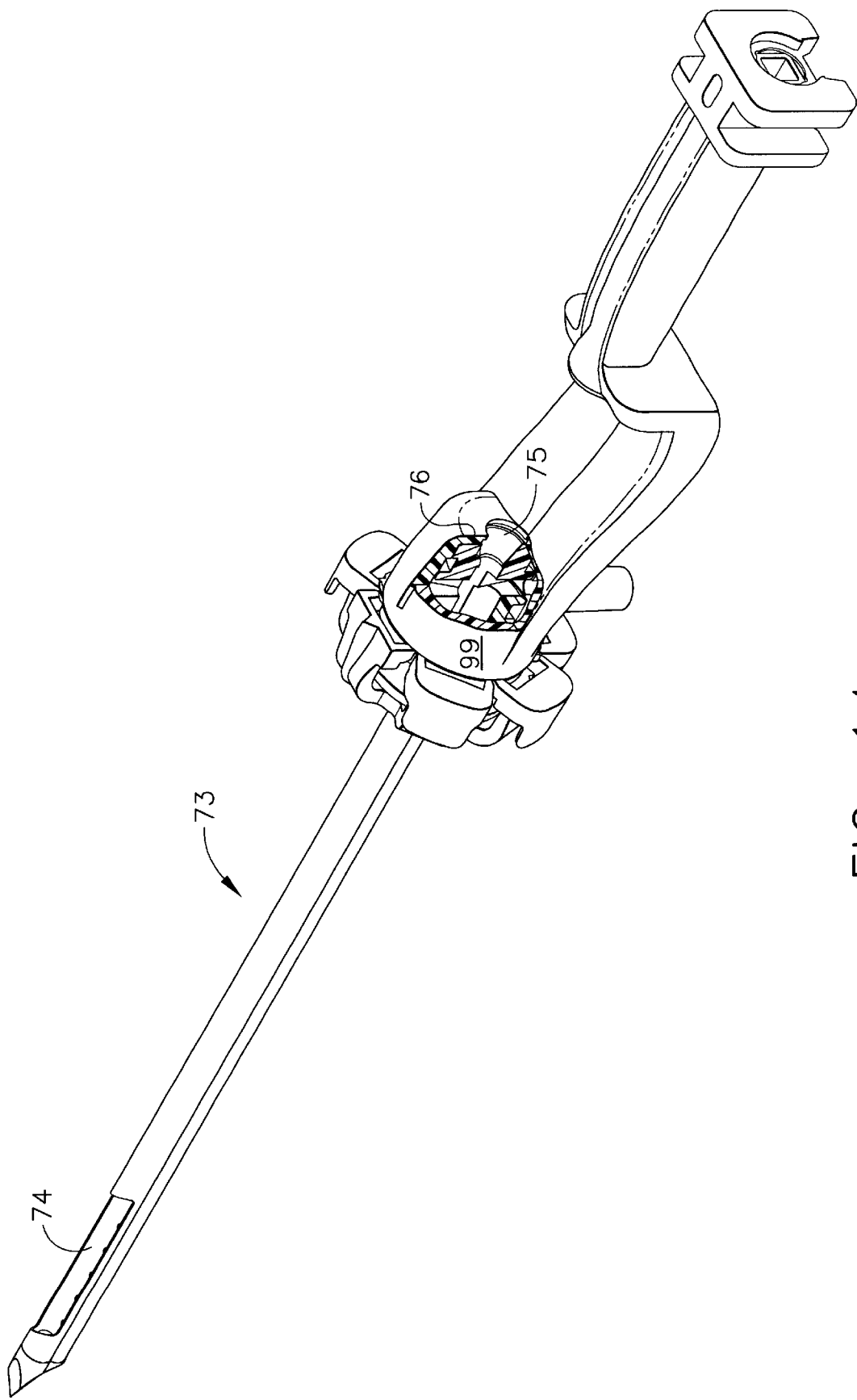
FIG. 14 is an isometric view of a biopsy cannula of an instrument for taking a breast biopsy, where a portion of the biopsy cannula housing is broken away to better illustrate the insertion and orientation of the egress tube into the biopsy cannula.

In FIG. 14, a conventional biopsy cannula 73 of a biopsy instrument which is used for extracting a tissue sample at a biopsy site is illustrated. The distal end of the biopsy cannula has an elongated biopsy port 74 which is adapted to receive the tissue sample. Near the proximal end of the biopsy cannula, there is a biopsy cannula housing 99 (partially broken away for ease of illustration) which includes a hub receiver 75 for receiving the alignment hub of the egress tube of the applier. More particularly, the hub receiver has an alignment tab receiver 76 for receiving the alignment tab of the alignment hub.

Figure 15:
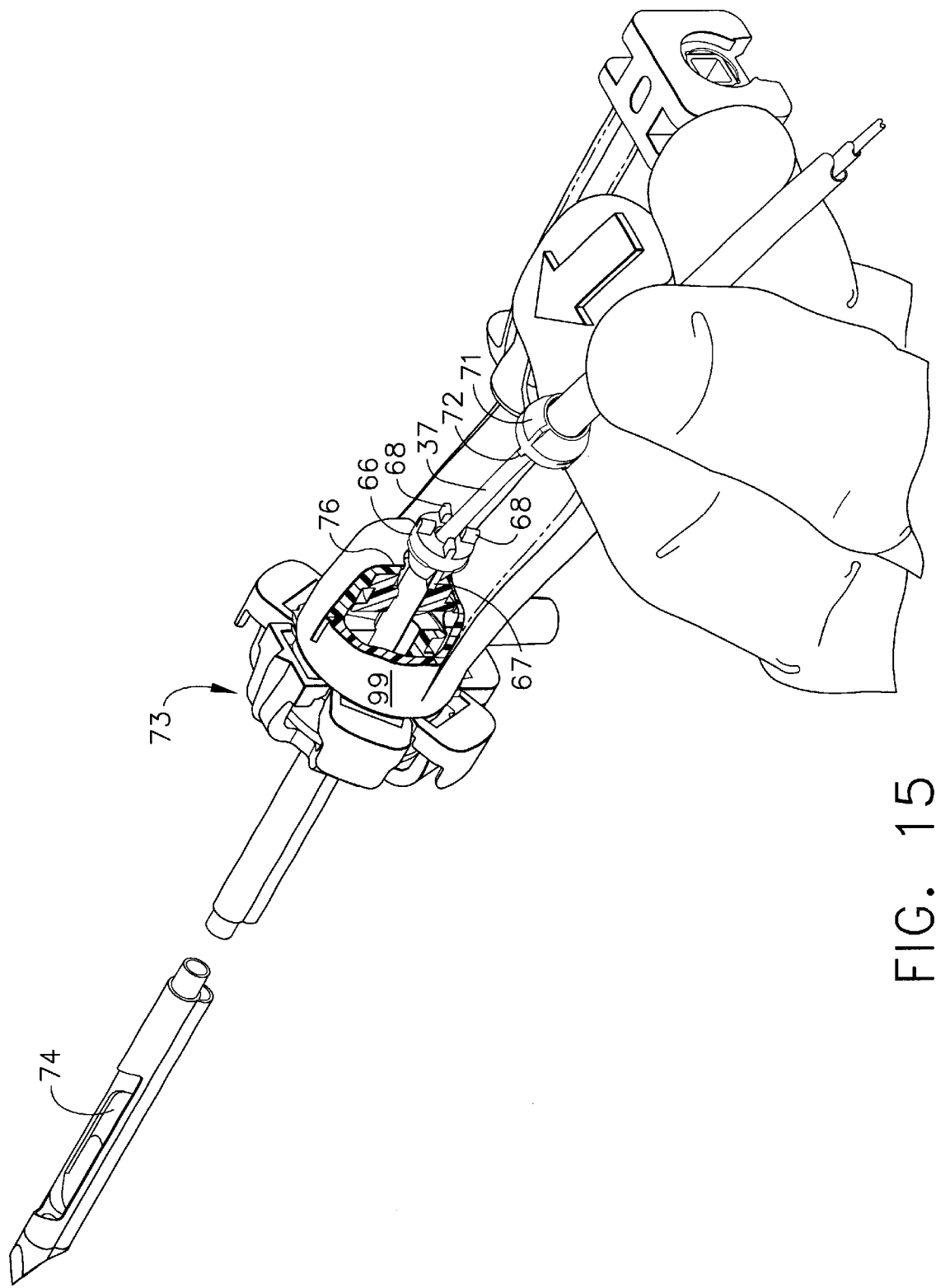
FIG. 15 is an isometric view illustrating insertion of the egress tube into the biopsy cannula of FIG. 14.
Figure 16:
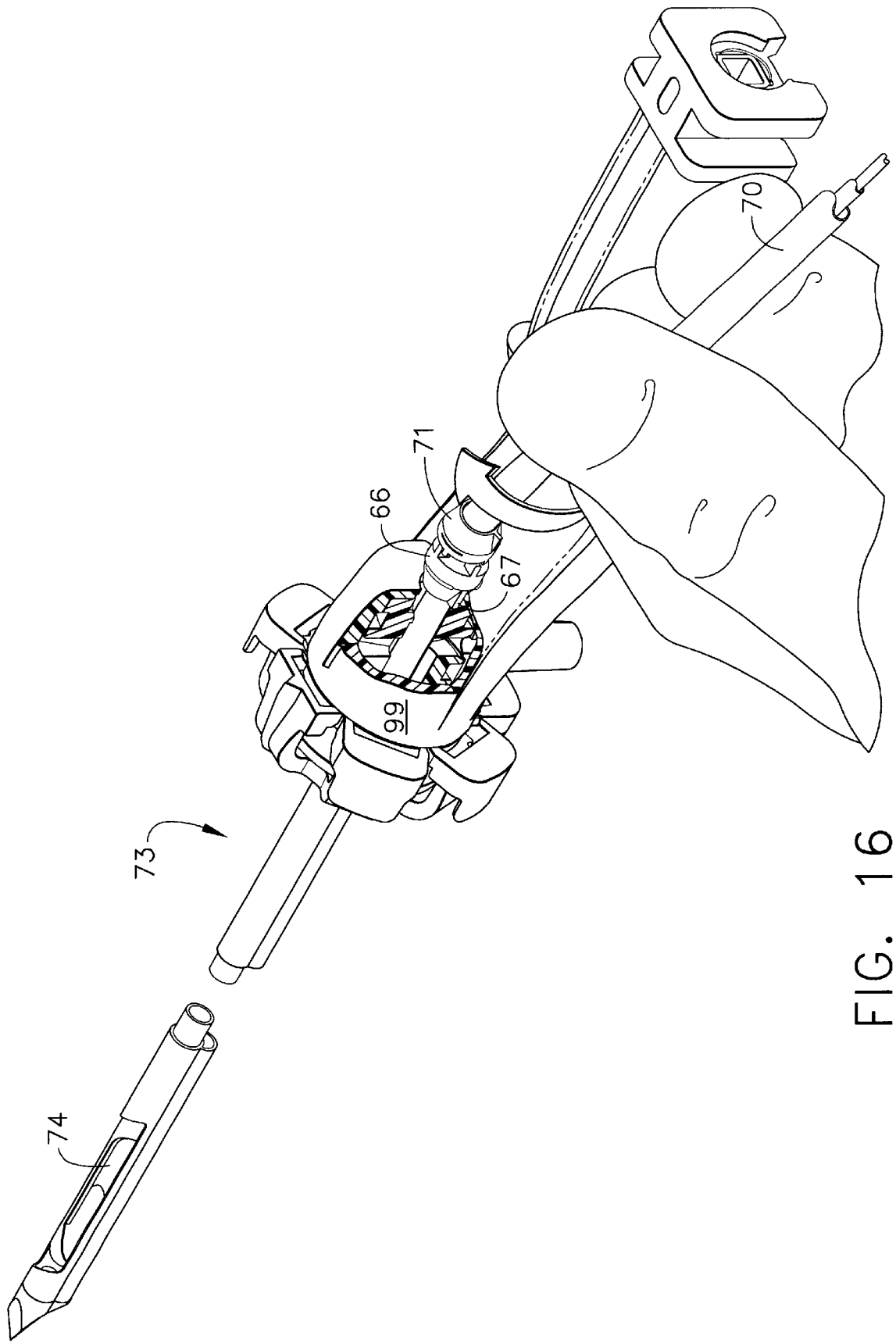
FIG. 16 is an isometric view illustrating the rotation of the alignment tool to align the alignment hub of the egress tube with the hub receiver of the biopsy cannula.
Figure 17:
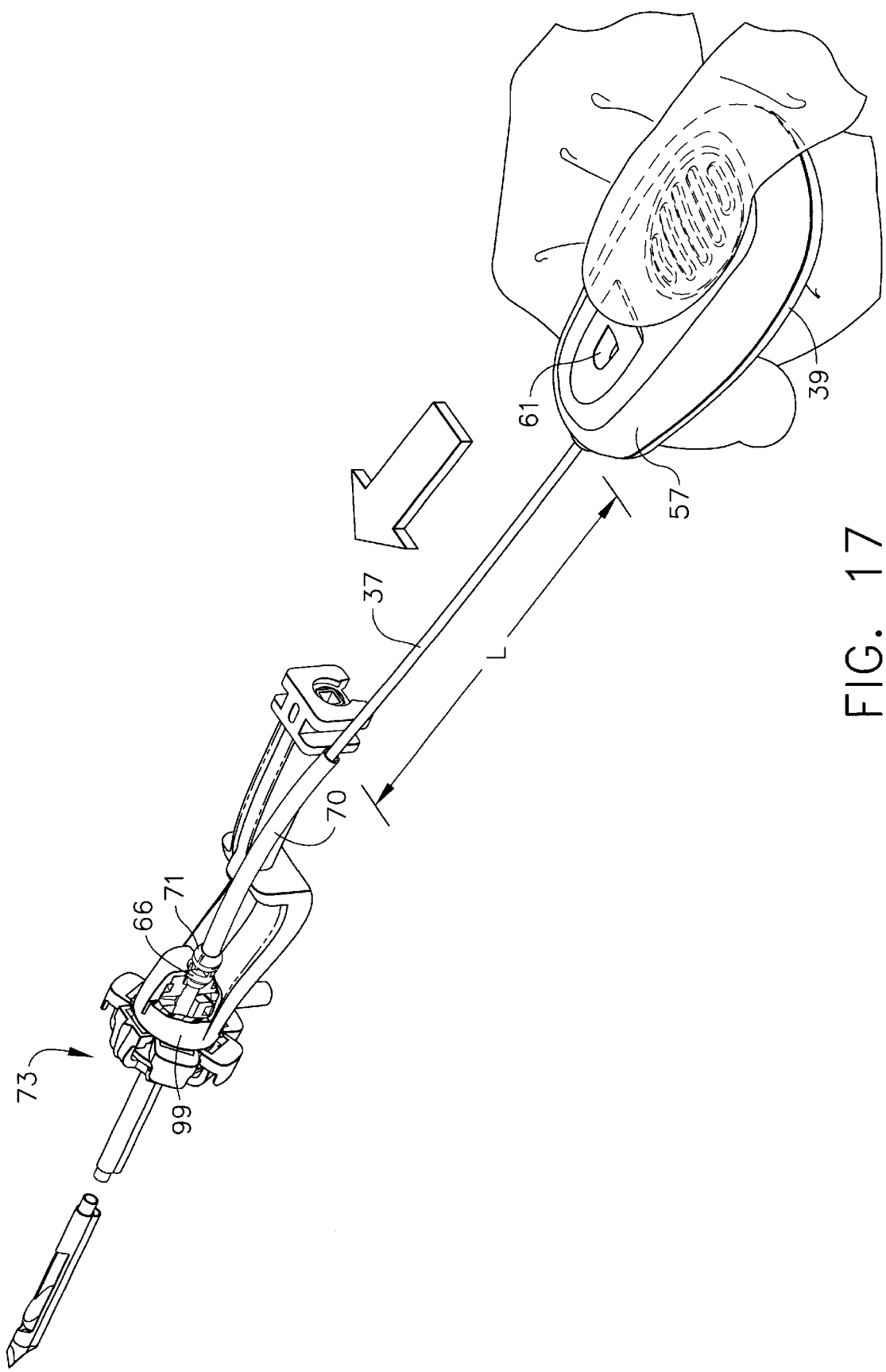
FIG. 17 is an isometric view of the applier having been aligned with the biopsy cannula of FIG. 14.
Figure 18:
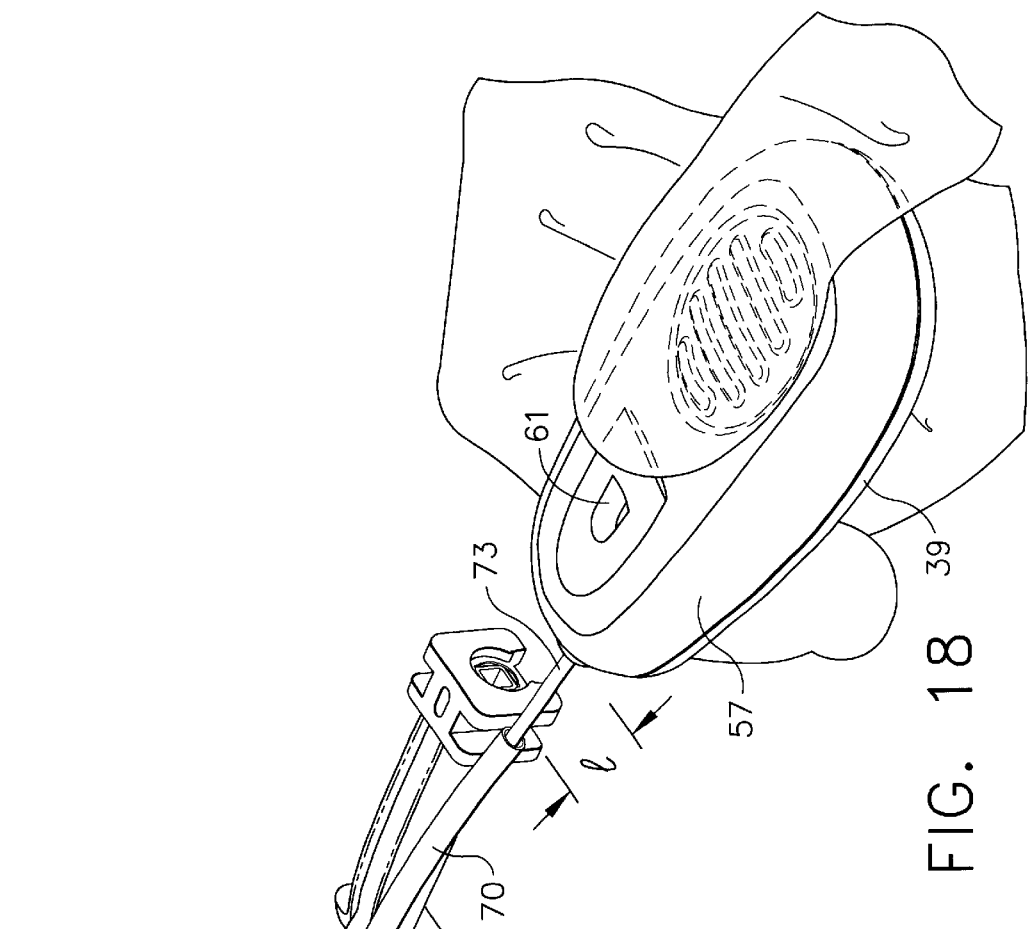
FIG. 18 is an isometric view of the applier with the housing portion of the applier moved distally until the marker and its ferrule are adjacent the base of an egress ramp at the egress opening of the egress tube.
Figure 19:
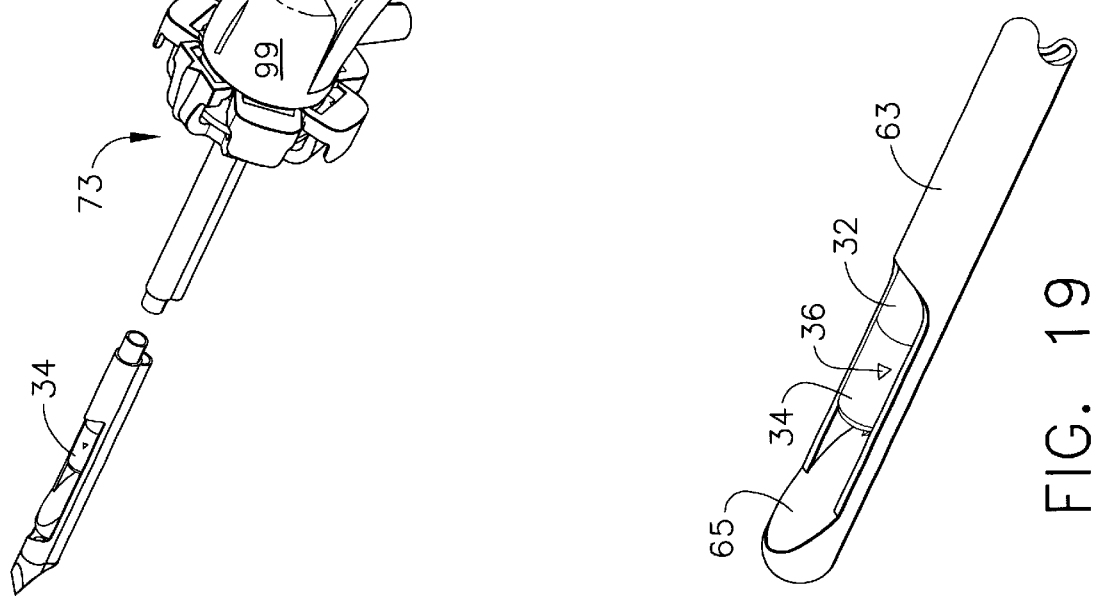
FIG. 19 is an enlarged isometric view of the distal portion of the egress tube of FIG. 18.

Referring now to FIGS. 15–18, once a portion of the distal end of the elongated flexible tube is threaded into the egress tube, the user can then insert the egress tube of the applier through the hub receiver of the biopsy cannula. When the alignment hub 66 of the egress tube abuts the hub receiver, the alignment tool is then moved distally toward the alignment hub as illustrated in FIG. 15. When the driver tabs 72 of the hub driver on the driver tube of the alignment tool are mated with the corresponding hub tabs 68 on the alignment hub of the egress tube, the user can then rotate the driver tube to correspondingly rotate the alignment hub. Consequently, the egress tube is likewise rotated. The rotation of the egress tube is necessary because it is critical that the egress opening at the distal end of the egress tube is aligned in the same direction as the biopsy port of the biopsy cannula. As the user rotates the driver tube of the alignment tool, the alignment hub is brought into proper alignment with the hub receiver when the alignment tab 67 is aligned with the alignment tab receiver 76 on the biopsy cannula. When this alignment is achieved, proper alignment of the egress opening 64 at the distal end of the egress tub with the biopsy port 74 of the biopsy cannula is assured. Once proper alignment is accomplished with the alignment tool, the user can then continue to insert the elongated flexible tube through the egress tube in the distal direction from the position designated as "L" in FIG. 17 to the position designated as "l" in FIG. 18. As illustrated in FIG. 19, the ferrule 34 is positioned adjacent the egress ramp 65 when the elongated flexible tube is positioned as shown in FIG. 18.

Figure 20:
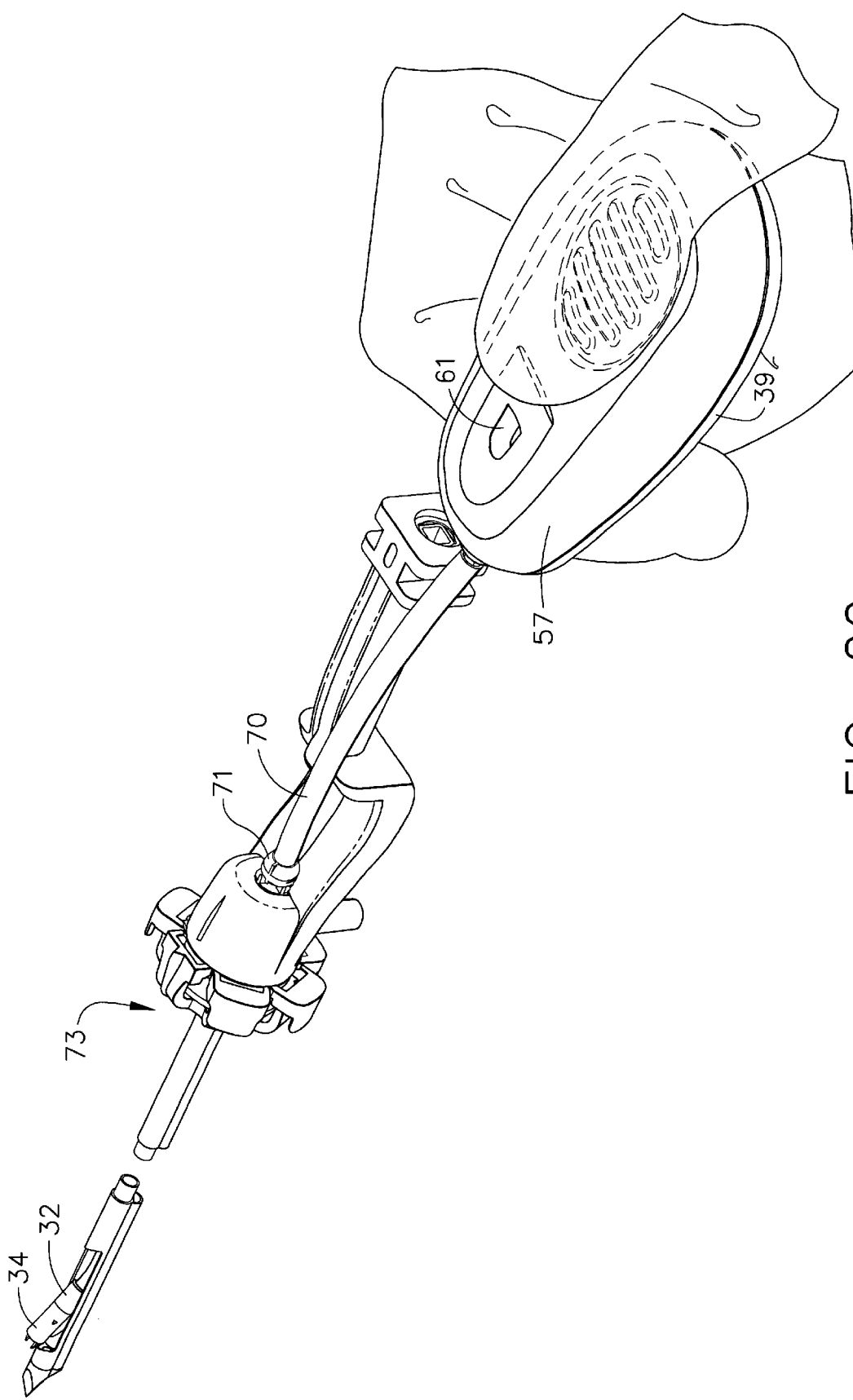
FIG. 20 is an isometric view of the applier with the housing portion at its distal most position illustrating the ramped movement of the marker and its ferrule up the egress ramp of the egress tube.
Figure 21:
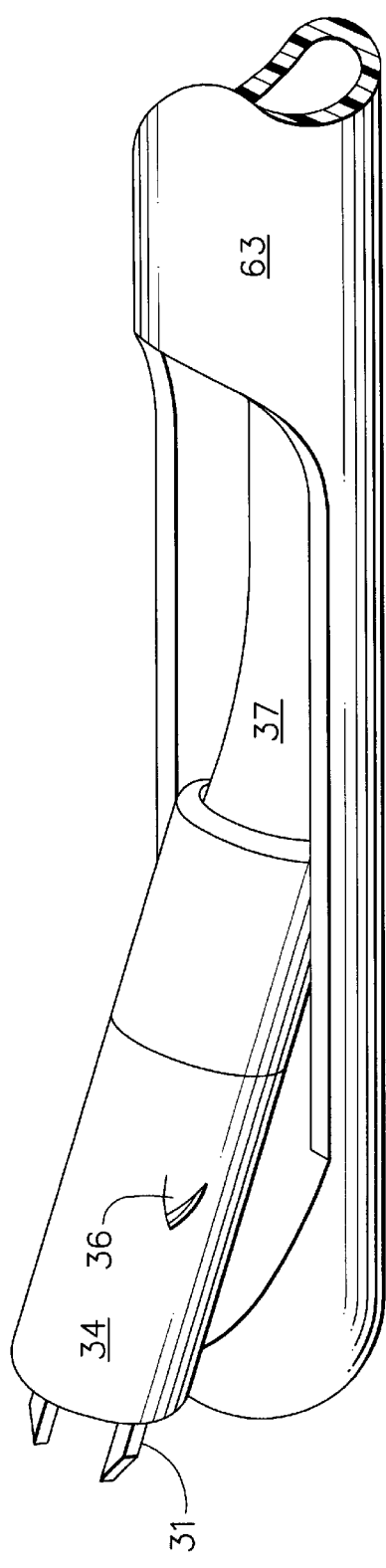
FIG. 21 is an enlarged isometric view of the distal portion of the egress tube of FIG. 20 where the marker is positioned for deployment
Figure 28:
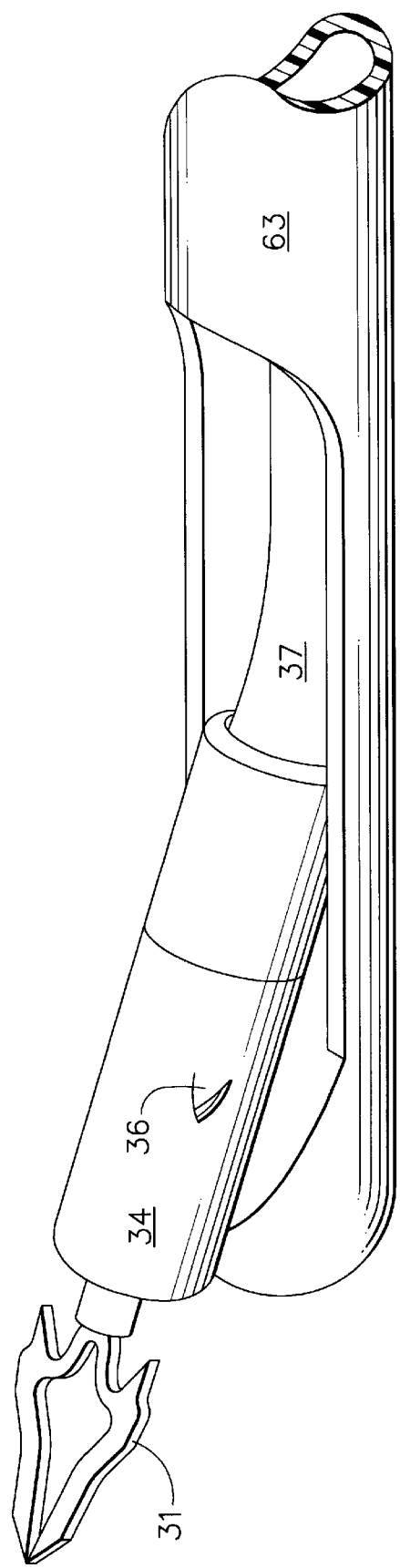
FIG. 28 is an enlarged isometric view of the distal portion of the egress tube after final deployment of the marker.
Figure 24:
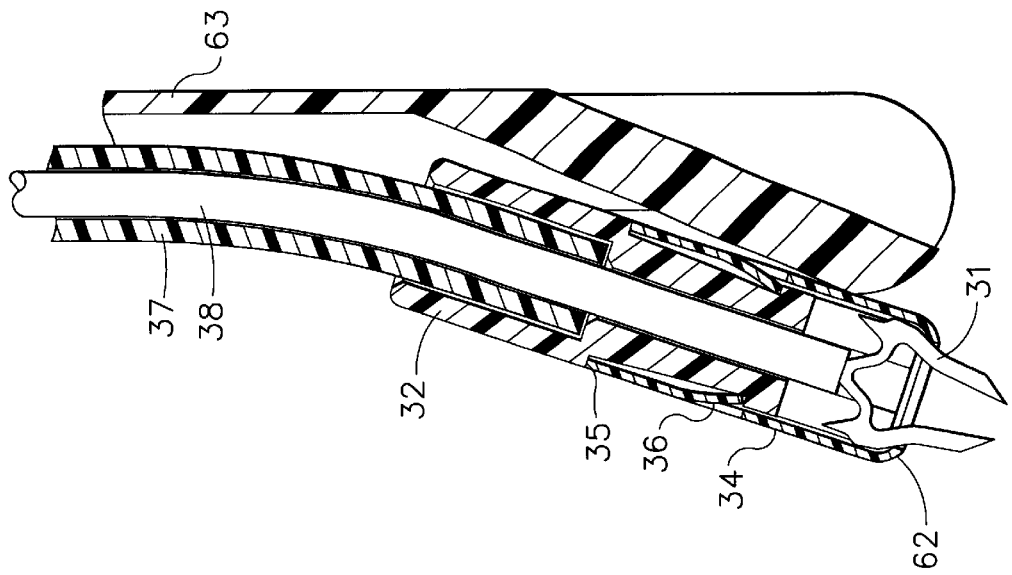
FIG. 24 is a fragmentary distal end sectional view illustrating the marker in a further stage of ejection from the applier.
Figure 23:
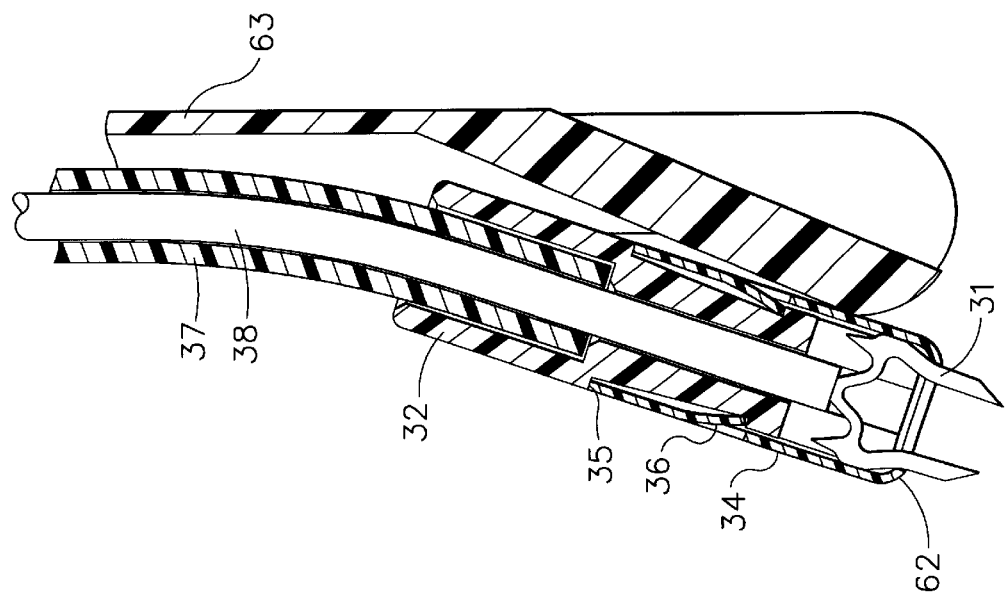
FIG. 23 is a fragmentary distal end sectional view illustrating the marker in its initial stage of ejection from the applier.
Figure 22:
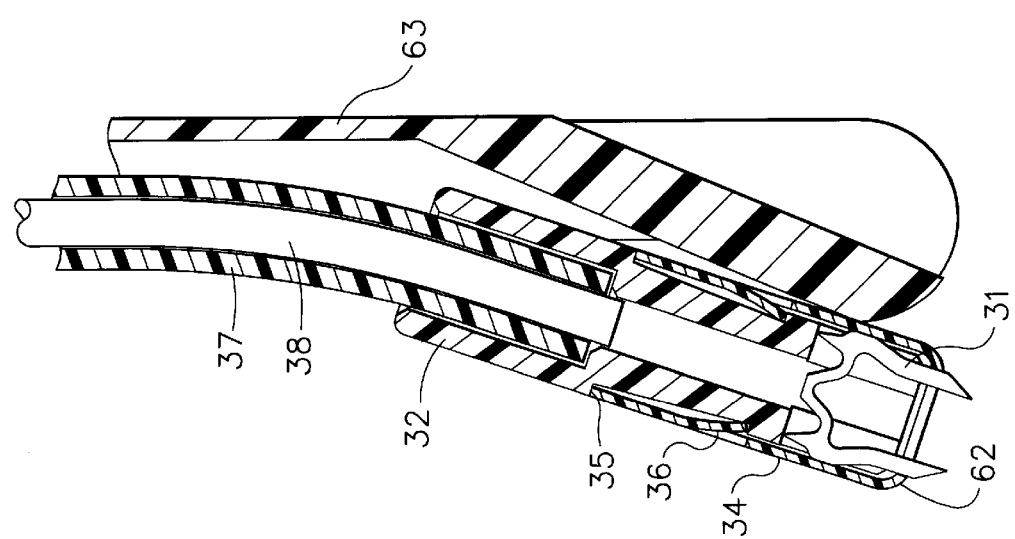
FIG. 22 is a fragmentary distal end sectional view illustrating the plan view of the marker loaded within the applier in its original open configuration.
Figure 27:
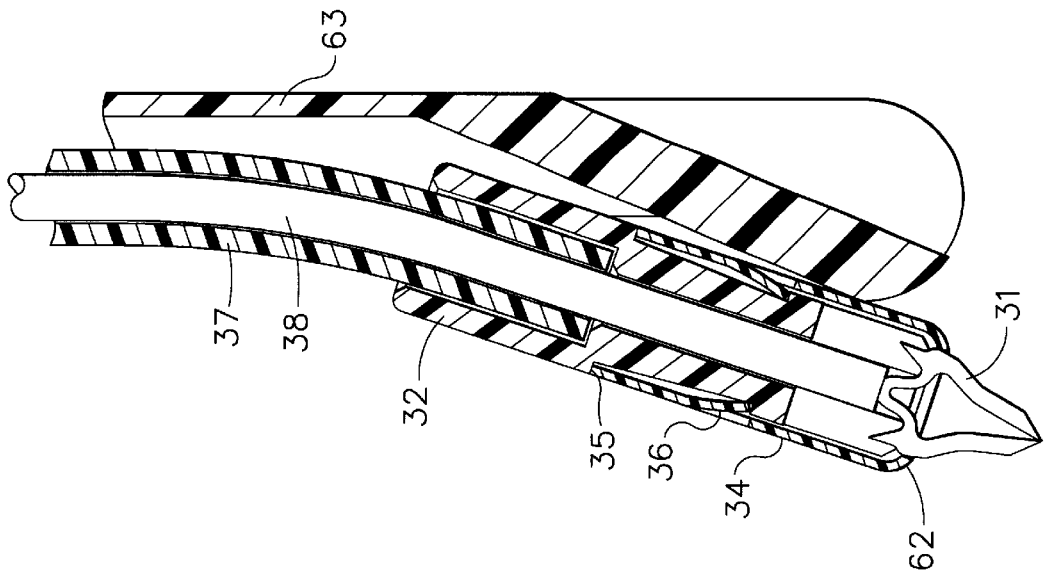
FIG. 27 is a fragmentary distal end sectional view illustrating the marker at a final stage of ejection just prior to release from the applier.
Figure 26:
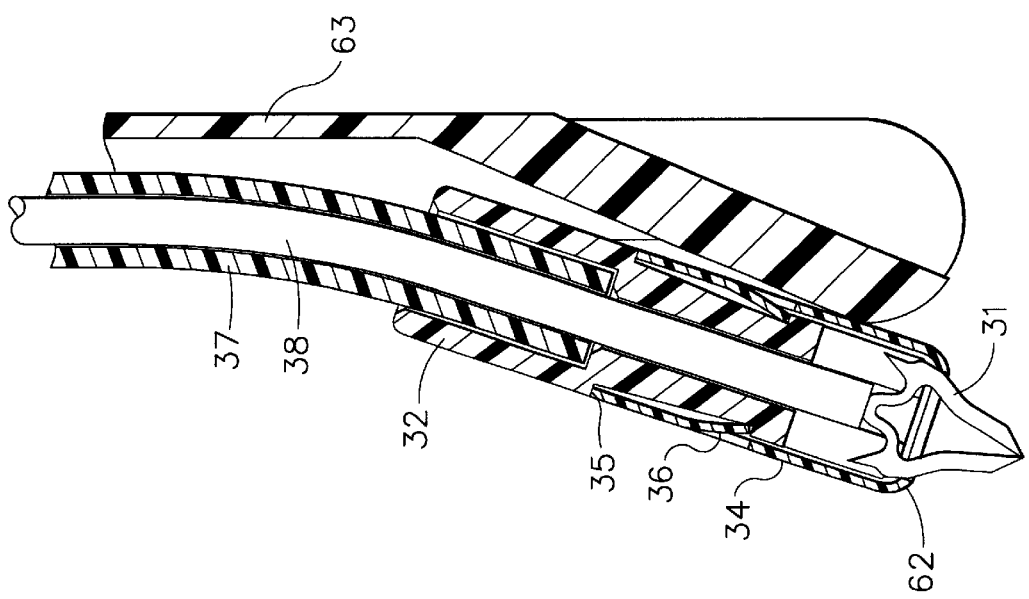
FIG. 26 is a fragmentary distal end sectional view illustrating the marker in a still further stage of ejection from the applier.
Figure 25:
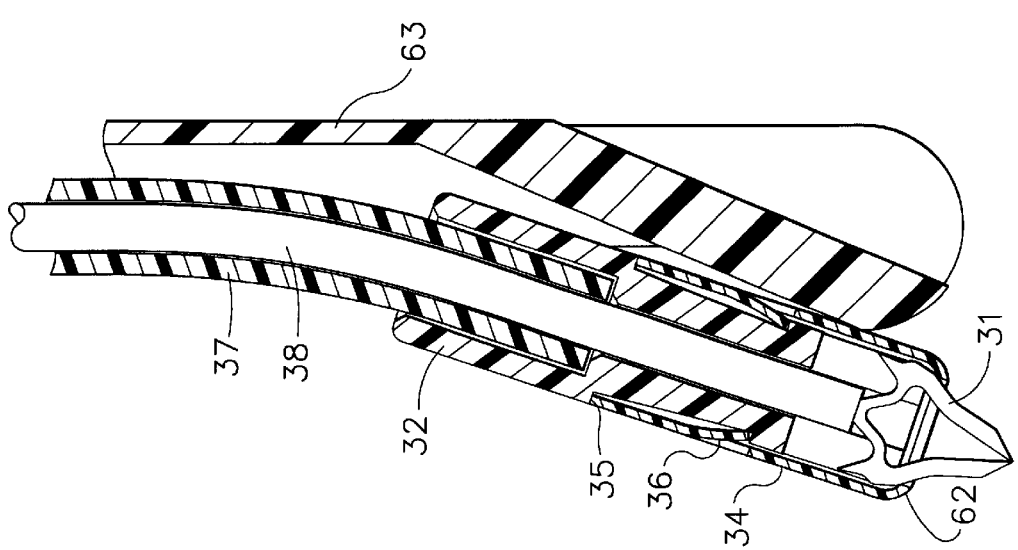
FIG. 25 is a fragmentary distal end sectional view illustrating the marker in yet a further stage of ejection from the applier.

As illustrated in FIGS. 20 and 21, when the user has moved the flexible tube distally so that the housing abuts the proximal end of the driver tube 70, the ferrule 34 has slid on the egress ramp so that the distal end of the flexible tube protrudes from the distal end of the egress tube for proper delivery and positioning at the biopsy site.

Once the marker is properly positioned where the ferrule of the applier protrudes from the distal end of the egress tube, and accordingly from the biopsy port of the biopsy cannula as well, the marker has now been delivered and properly positioned at the biopsy site. FIGS. 22–28 illustrate the sequence of steps as the push wire forming rod is moved from its unactuated position spaced from the marker to its fully actuated position where the forming rod and marker protrude from the distal end of the ferrule, and the marker has been reconfigured from its opened position to its closed position. As the forming rod moves distally in response to squeezing of the release button, it contacts the bridge of the marker and urges the marker through the ferrule. As the marker is urged through the ferrule, the legs of the marker are cammed against the rolled distal edge forming surface 62 of the ferrule. This camming action urges the tips of the legs of the marker together for proper deployment of the marker.

Although this invention has been described in connection with its most preferred embodiment, numerous additional embodiments will become apparent to those skilled in this art Accordingly, the reader should refer to the claims which appear below to understand the full scope and spirit of the claimed invention. The most preferred embodiment of this invention is intended solely to provide an example of the invention and not to limit the scope of the claimed invention.

What is claimed is:

1. An applier for initially delivering a biopsy marker to a surgical biopsy site and subsequently deploying said marker at the site, said applier comprising:

a) an elongated flexible tube having a distal end;
   b) a ferrule fixed to the distal end of said flexible tube, said ferrule having a forming surface thereon adapted to reconfigure said biopsy marker from an original open configuration to a closed configuration when said biopsy marker has been delivered to the surgical site;
   c) a marker holder at said ferrule for holding said biopsy marker at the distal end of said flexible tube in the original open position;
   d) an elongated forming rod located in said flexible tube, said forming rod adapted to urge said biopsy marker into reconfiguring contact with said forming surface of said ferrule, said forming rod slidable in said flexible tube from an unactuated position wherein said biopsy marker is in the original open position to an actuated position wherein said biopsy marker has been reconfigured in the closed position;
   e) an egress tube for receiving the distal end of said elongated flexible tube, said egress tube adapted for delivery through a biopsy cannula wherein said cannula has a biopsy port at a distal end thereof for positioning at the surgical biopsy site to take a biopsy sample, said egress tube having proximal and distal ends, said egress tube having an egress opening at the distal end of said egress tube and an alignment hub at the proximal end of said egress tube, said alignment hub adapted for orientational alignment with a hub receiver on said biopsy cannula so as to align said egress opening of said egress tube with said biopsy port of said biopsy cannula.

2. The applier of claim 1 wherein said elongated flexible tube has a proximal end, and further comprising a housing fixed to the proximal end of said flexible tube.

3. The applier of claim 2 further comprising an alignment tool mounted over said flexible tube for sliding and rotational movement between said housing and said alignment hub on said egress tube.

4. The applier of claim 3 wherein said alignment tool has a driver tube and a hub driver on a distal end of said driver tube, said hub driver capable of being coupled to said alignment hub of said egress tube, and said alignment hub is rotated for orientational alignment with said hub receiver on said biopsy cannula when said hub driver is coupled to said alignment hub and said driver tube is rotated.

5. The applier of claim 1 wherein said marker holder has a marker slot thereon for receiving said biopsy marker.

6. The applier of claim 2 wherein said housing contains a slider therein coupled to a proximal end of said forming rod, said slider movable from an unfired position to a fired position, and when said slider is moved from the unfired position to the fired position, said forming rod is moved from the unactuated position to the actuated position.

7. The applier of claim 6 wherein said housing has a housing cover covering said slider, said housing having a release button protruding from said housing cover, and when said release button is squeezed, said slider is triggered so as to move from the unfired position to the fired position.

8. The applier of claim 7 wherein said slider has an indicator tab, and said housing cover has a view port, and when said slider has moved to the fired position, said indicator tab is observable through said view port of said housing cover.

* * * * *